US008435679B2

(12) United States Patent
Lamanna et al.

(10) Patent No.: US 8,435,679 B2
(45) Date of Patent: May 7, 2013

(54) FLUORINATED COMPOUNDS FOR USE IN LITHIUM BATTERY ELECTROLYTES

(75) Inventors: William M. Lamanna, Stillwater, MN (US); Michael J. Bulinski, Houlton, WI (US); Michael G. Costello, Afton, MN (US); Jeffrey R. Dahn, Halifax (CA); Richard M. Flynn, Mahtomedi, MN (US); Yadong Wang, Wuhan (CN); Jing Li, Fairfax, VA (US); Lee Moshurchak, Halifax (CA)

(73) Assignee: 3M Innovative Properties Counsel, St. Paul, MN (US)

( * ) Notice: Subject to any disclaimer, the term of this patent is extended or adjusted under 35 U.S.C. 154(b) by 794 days.

(21) Appl. No.: 12/519,461

(22) PCT Filed: Dec. 12, 2007

(86) PCT No.: PCT/US2007/087114
§ 371 (c)(1),
(2), (4) Date: Dec. 9, 2009

(87) PCT Pub. No.: WO2008/079670
PCT Pub. Date: Jul. 3, 2008

(65) Prior Publication Data
US 2010/0104950 A1    Apr. 29, 2010

Related U.S. Application Data

(60) Provisional application No. 60/871,076, filed on Dec. 20, 2006.

(51) Int. Cl.
*H01M 6/16*    (2006.01)
(52) U.S. Cl.
USPC ........... 429/307; 429/341; 429/199; 429/200; 252/62.2
(58) Field of Classification Search .................. 429/307, 429/341, 199, 200; 252/62.2
See application file for complete search history.

(56) References Cited

U.S. PATENT DOCUMENTS

| | | | |
|---|---|---|---|
| 3,359,296 | A | 12/1967 | Newallis et al. |
| 5,659,062 | A | 8/1997 | Yokoyama et al. |
| 5,891,588 | A | 4/1999 | Sakai et al. |
| 5,916,708 | A | 6/1999 | Besenhard et al. |
| 5,925,283 | A | 7/1999 | Taniuchi et al. |
| 6,010,806 | A | 1/2000 | Yokoyama et al. |
| 6,210,835 | B1 | 4/2001 | Arai |
| 6,696,202 | B2 | 2/2004 | Arai |
| 6,984,471 | B2 | 1/2006 | Suzuki et al. |
| 2005/0227143 | A1 | 10/2005 | Amine et al. |
| 2008/0145763 | A1 | 6/2008 | Koh et al. |

FOREIGN PATENT DOCUMENTS

| | | |
|---|---|---|
| EP | 0 807 986 | 5/1996 |
| EP | 1 039 570 | 9/2000 |
| JP | 6003737 | 1/1994 |
| JP | 7-249432 | 9/1995 |
| JP | 9-147911 | 6/1997 |
| JP | 9-148197 | 6/1997 |
| JP | 9-180721 | 7/1997 |
| JP | 10-116629 | 5/1998 |
| JP | 10-116630 | 5/1998 |
| JP | 10-144346 | 5/1998 |
| JP | 10-189046 | 7/1998 |
| JP | 10-233345 | 9/1998 |
| JP | 10-247519 | 9/1998 |
| JP | 10-321479 | 12/1998 |
| JP | 11-40195 | 2/1999 |
| JP | 11-176472 | 7/1999 |
| JP | 11-260402 | 9/1999 |
| JP | 11-307120 | 11/1999 |
| JP | 2000-26373 | 1/2000 |
| JP | 2000-150317 | 5/2000 |
| JP | 2000-195544 | 7/2000 |
| JP | 2000-228216 | 8/2000 |
| JP | 2000-327634 | 11/2000 |
| JP | 2000-344763 | 12/2000 |
| JP | 2002-343424 | 11/2002 |
| JP | 2002-373702 | 12/2002 |
| JP | 2003-17066 | 1/2003 |
| JP | 2003-217656 | 7/2003 |
| JP | 2004-71245 | 3/2004 |
| JP | 2004-281185 | 10/2004 |
| JP | 2005-47875 | 2/2005 |
| JP | 2005-60261 | 3/2005 |
| JP | 2005-71678 | 3/2005 |
| JP | 2005-78820 | 3/2005 |
| JP | 2007-305352 | 11/2007 |
| WO | 2005/123656 | 12/2005 |
| WO | 2006/021452 | 3/2006 |
| WO | WO 2006/088009 | 8/2006 |
| WO | 2006/106655 | 10/2006 |
| WO | 2006/106657 | 10/2006 |

OTHER PUBLICATIONS

Nakajima et al., "Effect of addition of fluoroethers to organic solvents for lithium ion secondary batteries", *Journal of Fluorine Chemistry* 111 (2001) pp. 167-174.
Kyokane et al., "Electrical properties of fluorinated gel electrolytes using high ionic conducting solution and its application to secondary battery", *Thin Solid Films* 438-439 (2003) pp. 257-261.
Nakajima, "Fluorine-containing energy conversion materials", *Journal of Fluorine Chemistry* 105 (2000) pp. 229-238.
Nagasubramanian, "Fluoro-Carbonate Solvents for Li-Ion Cells", Electrochemical Society Proceedings, vol. 99-25, pp. 434-439.
Smart et al., "Improved performance of lithium-ion cells with the use of fluorinated carbonate-based electrolytes", *Journal of Power Sources* 119-121 (2003) pp. 359-367.
Supplementary Search Report for EP Application No. 0769119.3, PCT/US2007/087114, p. 10.
Koh, M. et al., "Synthesis and electrochemical properties of the fluorine containing polymer electrolytes," Polymer Reprints, vol. 46, No. 2, (2005), p. 650.
Australian Patent Office Search Report for Application No. SG 200904223-5, Application Filing Date: Dec. 12, 2007.

*Primary Examiner* — Laura Weiner
(74) *Attorney, Agent, or Firm* — Dean M. Harts; Adam Bramwell

(57) ABSTRACT

Provide are fluorinated cyclic and acyclic carbonate solvent compositions such as various fluorine substituted 1,3-dioxolane-2-one compounds and fluorine substituted 1,3-dioxane-2-one compounds, which are useful as electrolyte solvents for lithium ion batteries.

4 Claims, No Drawings

FLUORINATED COMPOUNDS FOR USE IN LITHIUM BATTERY ELECTROLYTES

CROSS REFERENCE TO RELATED APPLICATION

This application claims the benefit of U.S. Provisional Patent Application No. 60/871,076, filed Dec. 20, 2006, the disclosure of which is incorporated by reference herein in its entirety.

TECHNICAL FIELD

This disclosure relates to electrolyte compositions comprising at least one partially-fluorinated compound and at least one electrolyte salt. In other aspects, this disclosure also relates to electrochemical devices comprising the electrolyte compositions and to articles comprising the electrochemical devices.

BACKGROUND

The rapid development of electronic devices has increased market demand for electrochemical devices such as fuel cells and battery systems. In response to the demand for battery systems in particular, practical, rechargeable lithium batteries have been actively researched. Lithium-ion batteries are particularly useful for many portable electronic devices. Lithium-ion batteries employ highly chemically reactive components to provide electrical current. These systems are typically based on the use of lithium metal, lithiated carbon, or a lithium alloy as the negative electrode (anode) and electroactive transition metal oxides as the positive electrode (cathode).

Lithium-ion batteries are constructed from one or more electrochemical cells connected in parallel or series. Such cells have consisted of a non-aqueous lithium ion-conducting electrolyte composition interposed between electrically-separated and spatially-separated, positive and negative electrodes. The electrolyte composition is typically a liquid solution of a lithium salt in a nonaqueous, aprotic organic solvent. A mixture of two or more organic solvents often is used.

The selection of electrolyte solvents for rechargeable lithium batteries is important for optimum battery performance and safety and involves a variety of different factors. However, long-term chemical stability in the presence of the charged positive and negative electrodes, ionic conductivity, safety, and wetting capability tend to be important selection factors in high volume commercial applications.

Long-term chemical stability requires that an electrolyte solvent be intrinsically stable over the battery's range of operating temperatures and voltages and also that it be either unreactive with electrode materials or that it contribute to effectively forming a passivating film with good ionic conductivity on the electrodes. Ionic conductivity requires an electrolyte solvent that effectively dissolves lithium electrolyte salts and facilitates lithium ion mobility. From the viewpoint of safety, the characteristics of low volatility, low flammability, low combustibility, low reactivity toward charged electrodes, passivating characteristics, and low toxicity are all highly desirable. It is also desirable that the battery's electrodes and separator be quickly and thoroughly wetted by the electrolyte solvent, so as to facilitate rapid battery manufacturing and optimize battery performance.

Aprotic liquid organic compounds have been the most commonly used electrolyte solvents for lithium batteries. Often, compounds such as carbonic acid esters (carbonates) have been used, as these compounds typically share the desirable properties of low reactivity with the positive electrodes operating at less than about 4.4V vs. $Li^+/Li$, low reactivity with lithium-containing negative electrodes, and a thermodynamically favorable solvation interaction with lithium salts, which results in the electrolyte composition having a high ionic conductivity.

The most commonly used aprotic organic electrolyte solvents for use in lithium batteries include cyclic carbonates such as ethylene carbonate and propylene carbonate, cyclic esters of carboxylic acids such as γ-butyrolactone, linear carbonates such as dimethyl caronate, diethyl carbonate and ethyl methyl carbonate, cyclic ethers such as 2-methyltetrahydrofuran and 1,3-dioxolane, linear ethers such as 1,2-dimethoxyethane, amides, and sulfoxides. A mixed solvent is often preferred in order to balance, or tailor, the desired properties of the electrolyte composition such as high dielectric constant and low viscosity.

Drawbacks to the use of conventional lithium battery electrolyte solvents are generally related to their properties such as low boiling points and high flammability or combustibility. Some solvents, such as ethylene carbonate and propylene carbonate, have boiling points above 200° C. However, many electrolyte solvents have boiling points that are substantially lower and have flash points less than 30.2° C. (100° F.). Such volatile solvents can ignite during catastrophic failure of a fully or partially charged battery that has undergone, for example, a rapid discharge due to a short circuit. Additionally, volatile solvents present difficulties in the preparation and storage of electrolyte compositions as well as in the addition of the electrolyte composition to the battery during the manufacturing process. Also, many conventional battery electrolyte solvents are reactive towards charged electrodes at elevated temperatures, which can result in thermal runaway under abuse conditions. In fact, recent news reports noted that overheating and even spontaneous combustion of secondary batteries have led to product recalls.

SUMMARY

The present inventors noted that non-aqueous electrolyte solutions for lithium ion batteries should have a low viscosity to allow for high ion mobility during high rates of charging and discharging.

The present inventors recognize that there remains a need for electrolyte solvents with one or more of various advantages, such as reduced volatility, low flammability, and low combustibility relative to conventional solvents, that are less reactive with the charged positive electrode and the charged negative electrode, and that effectively dissolve and dissociate salts to form stable electrolyte compositions that adequately wet electrochemical device components and that exhibit adequate ionic conductivities over a range of operating temperatures. Preferably, various embodiments of the present invention have a combination of these advantages. Some embodiments of the present invention may have all of these advantages.

Briefly, in one aspect, provided is a solvent composition according to Formula I:

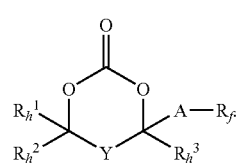

I wherein each of the groups $R_h^1$, $R_h^2$ and $R_h^3$ is independently hydrogen or $C_xH_{2x+1}$, x is an integer from 1 to 4, Y is a single covalent bond or the group —$CR_h^4R_h^5$—, each of $R_h^4$ and $R_h^5$ is independently a hydrogen or an alkyl group having 1 to 4 carbon atoms. Also in this formula, $R_f$ is —$CFR_f^1CHFR_f^2$, wherein $R_f^1$ is F, or $C_nF_{2n+1}$, and n is an integer from 1 to 8, $R_f^2$ is F, a linear or branched $C_pF_{2p+1}$, wherein p is an integer from 1 to 4, or $R_f^3O(R_f^4O)_m$, wherein m is 0 or 1, and $R_f^3$ is $C_nF_{2n+1}$, and n is an integer from 1 to 8, and $R_f^4$ is $C_qF_{2q}$, wherein q is an integer from 1 to 4, provided that when $R_f^1$ is F and $R_f^2$ is F, then at least one of $R_h^1$, $R_h^3$ and $R_h^a$ is $C_xH_{2x+1}$, and wherein A is a single covalent bond or $CH_2O$.

Briefly, in another aspect, provided is a solvent composition according to the formula R—O—C(=O)—O—R', wherein at least one of R and R' is —$C(R_h^7)(R_h^8)_nCFR_f^1(CF_2CF_2)_nCHFR_f^7$, wherein $R_f^7$ is F, $C_nF_{2n+1}$, or $R_f^3O(R_f^4O)$ m—, n is 0 or 1, m is 0 or 1, and $R_h^8$ and $R_h^7$ are alkyl groups having 1 to 4 carbon atoms, and wherein $R_h^7$ and $R_h^8$ may together form a ring, provided that when n is 1 both $R_f^1$ and $R_f^7$ are fluorine.

It has been discovered that at least some of the above-described novel partially fluorinated carbonate compounds have surprisingly high boiling points and low volatilities and thus, in general, are less flammable or less combustible than conventional electrolyte solvents. Yet solvent compositions including the compounds may also quite effectively dissolve electrolyte salts to provide electrolyte compositions that adequately wet electrochemical device components (such as separators) and that exhibit adequate ionic conductivities for use in electrochemical devices over a range of operating temperatures (for example, from about −20° C. to about 80° C. or even higher, depending upon the power requirements for a particular application). The solvent compositions (and electrolyte compositions including the solvent compositions) also can present fewer difficulties in storage and handling than do some conventional materials, due to one or more relative advantages such as lower volatility, lower flammability, and/or lower combustibility of the inventive partially fluorinated carbonate compounds and electrolyte compositions.

At least some of the partially fluorinated carbonate compounds are particularly well-suited for use in large format lithium ion batteries (batteries that operate essentially adiabatically and can therefore experience high temperatures, for example, temperatures above 60° C.). In such batteries, electrolyte compositions comprising the compounds of the invention can exhibit adequate conductivities, while being less likely to react with charged electrodes or ignite during catastrophic battery failure than some conventional electrolyte compositions.

Thus, at least some solvent compositions including the partially fluorinated carbonate compounds meet a need for electrolyte solvents that have reduced reactivity, volatility, flammability, and combustibility (relative to conventional solvents), yet effectively dissolve electrolyte salts to form stable electrolyte compositions that adequately wet electrochemical device components and that exhibit adequate ionic conductivities over a range of operating temperatures.

In other aspects, this invention also provides electrochemical devices (preferably, batteries) including the electrolyte compositions; and articles including the electrochemical devices.

In one embodiment, fluorine substituted 1,3-dioxolane-2-one compounds are provided as electrolyte solvents for lithium ion batteries. In another embodiment, fluorine substituted 1,3-dioxane-2-one compounds are provided as electrolyte solvents for lithium ion batteries. In another embodiment, fluorine substituted acyclic carbonates are provided as electrolyte solvents for lithium ion batteries.

In another embodiment, mixtures of one or more fluorinated compounds of the invention together with non-fluorinated cyclic carbonates, acyclic carbonates, more conventional solvents, or combinations thereof, are provided as electrolytes for lithium ion batteries. In yet another embodiment, the invention provides a lithium ion battery with a fluorinated carbonate compound or a mixture of fluorinated carbonate compounds, optionally with non-fluorinated cyclic carbonates and acyclic carbonates and/or a conventional battery solvent as the electrolyte solvent package.

The electrolyte composition of the present invention provides low reactivity towards charged positive electrodes and charged negative electrodes and low flammability. The high boiling points of the electrolyte compositions of the present invention result in less pressure buildup in the cells at operating temperatures.

Other features and advantages of the invention will be apparent from the following detailed description of the invention and the claims. The above summary of principles of the disclosure is not intended to describe each illustrated embodiment or every implementation of the present disclosure. The figures and the detailed description that follow more particularly exemplify certain preferred embodiments using the principles disclosed herein.

DETAILED DESCRIPTION OF PRESENTLY PREFERRED EMBODIMENTS

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

A non-aqueous electrolyte solvent should have one or more, preferably several desirable properties. Examples follow. A non-aqueous electrolyte solvent should have low flammability or even be nonflammable. A non-aqueous electrolyte solvent can be nonflammable by having low volatility and/or by being very slow to react with oxygen. One quantitative measure of flammability is flash point. Another measure of flammability involves bringing a lighted match near a weighing pan containing the solvent of interest and observing whether ignition occurs. More details on this measure are found below in the Test Method section. Preferably a formulated electrolyte solution has a flash point above the operating temperature of a battery in which the electrolyte is used. The operating temperature of such batteries is normally around 60° C. A non-aqueous electrolyte should allow the cell to be charged and discharged (cycled) without losing capacity after each consecutive cycle.

A non-aqueous electrolyte should be electrochemically stable at highly reducing and oxidizing potentials. The threshold for electrochemical oxidation of the non-aqueous electrolyte should be at a voltage (versus $Li^+/Li$) that is greater than the cathode (positive electrode) voltage at full state of charge. The threshold for electrochemical reduction of the non-aqueous electrolyte should be at a voltage that is lower (versus $Li^+/Li$) than the anode (negative electrode) voltage at full state of charge.

A non-aqueous electrolyte solvent should be chemically stable to the charged, active cathode material and to the charged, active anode material. One measure of stability is the exotherm onset temperature of the reaction between the non-aqueous electrolyte and the charged, active cathode material or the charged, active anode material as determined by accelerating rate calorimetry (ARC).

However, some limited oxidation or reduction or chemical reaction of the non-aqueous electrolyte at the electrode surface can be beneficial if a passivating Solid Electrolyte Interface (SEI) layer is formed in the process. This SEI layer can protect the electrolyte from further reaction with the electrodes.

In one aspect, the present invention provides cyclic carbonate compositions having structures according to Formula I:

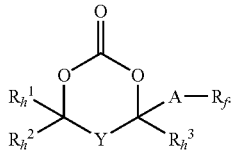

I

In Formula I, each of the groups $R_h^1$, $R_h^2$ and $R_h^3$ is independently hydrogen or $C_xH_{2x+1}$, wherein x is an integer from 1 to 4, and Y is a covalent bond or the group $-CR_h^4R_h^5$ where each of $R_h^o$ and $R_h^5$ is independently H or an alkyl group having 1 to 4 carbon atoms.

In Formula I, $R_f$ can be the partially fluorinated alkyl group $-CFR_f^1CHFR_f^2$, wherein $R_f^1$ is F, or $C_nF_{2n+1}$, and n is an integer from 1 to 8. In some embodiments, n is an integer from 1 to 6 and in other embodiments, most preferably n is an integer from 1 to 4. $R_f^2$ is F, $C_pF_{2p+1}$, wherein p is an integer from 1 to 4 and $C_nF_{2n+1}$, may be linear or branched, or $R_f^3O(R_f^4O)_m-$, wherein m is 0 or 1, and $R_f^3$ is $C_nF_{2n+1}$ wherein n is an integer from 1 to 8, and wherein $R_f^4$ is $C_qF_{2q}$ wherein q is an integer of 1 to 4. In some embodiments, n is an integer from 1 to 6 and in other embodiments, more preferably n is an integer from 1 to 4. $R_f^3$ and $R_f^4$ may be branched. In some embodiments, $R_f^2$ is $C_nF_{2n+1}$ or $R_f^3O(R_f^4O)_m-$. In the formula above, when $R_f^1$ is F and $R_f^2$ is F, then at least one of $R_h^1$, $R_h^2$ and $R_h^3$ is $C_xH_{2x+1}$.

In Formula I, A can be a single covalent bond or $CH_2O$. Preferably, in Formula I when A is $CH_2O$, then Y is a single covalent bond.

More particular cyclic carbonate electrolyte solvent materials are shown in Formula II and III, below, wherein the substituents are as defined above.

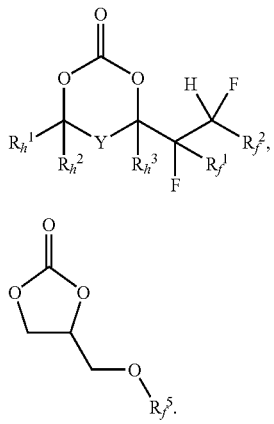

II

III

In another aspect, the present invention provides acyclic carbonate compositions having structures according to Formula IV:

R—O—C(=O)—O—R'  IV.

One more particular embodiment wherein R is $R_h^6$, and R' is $C(R_h^7)(R_h^8)_nCFR_f^1(CF_2CF_2)_nCHFR_f^7$ involves the composition of Formula V:

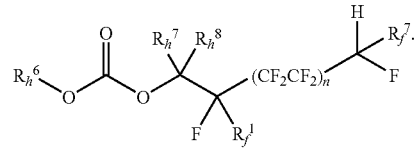

V

In Formula V, $R_h^6$ is $C_xH_{2x+1}$ and x is an integer from 1 to 4. $R_h^7$ and $R_h^8$ are independently hydrogen or an alkyl group comprising 1 to 4 carbon atoms and n is 0 or 1. $R_f^7$ can be F, a linear or branched $C_pF_{2p+1}$ group, where p is an integer from one to four or $R_f^7$ can be $R_f^3O(R_f^4O)_m-$. When $R_h^7$ and $R_h^8$ are both hydrogen, then n is 0 and $R_f^7$ is either a linear or branched $C_nF_{2n+1}$ group, where n is an integer from one to four or $R_f^7$ is $R_f^3O(R_f^4O)_m-$. When at least one of $R_h^7$ and $R_h^8$ is an alkyl group, then n may be 0 or 1. When n is 1, then at least one of $R_h^7$ and $R_h^8$ is an alkyl group and $R_f^1$ and $R_f^7$ are both F. When at least one of $R_h^7$ and $R_h^8$ is an alkyl group, and n is 0, then $R_f^1$ is F, or $C_nF_{2n+1}$ and $R_f^7$ is F, $C_pF_{2p+1}$ or $R_f^3O(R_f^4O)_m-$, as described above. When both $R_h^7$ and $R_h^8$ are alkyl groups, they may together form a ring having from 5 to 6 carbon atoms. A few exemplary electrolyte solvent structures are shown below in Formulas VI through VIII:

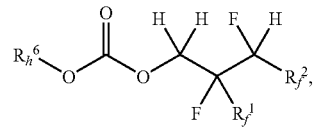

VI

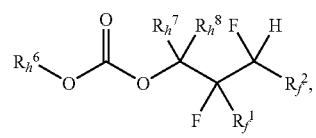

VII

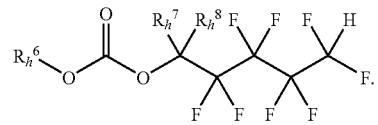

VIII

In another embodiment of ROC(O)OR', R and R' may each be independently represented by group $C(R_h^7)(R_h^8)_nCFR_f^1(CF_2CF_2)CHFR_f^7$. The structures represented by this embodiment may be symmetrical when R and R' are the same, or the structures may be asymmetrical (when R and R' are different). In each of the groups R and R', each $R_h^7$ and each $R_h^8$ is independently a hydrogen or an alkyl group comprising 1 to 4 carbon atoms, n may be zero or one, and at least one of $R_h^7$ and $R_h^8$ in R or R' is an alkyl group. When n is one then $R_f^1$ and $R_f^7$ are both F. Where both $R_h^7$ and $R_h^8$ are alkyl groups, they may be linked to form a ring of from 5 to 6 carbon atoms.

In another aspect, provided is an electrolyte solvent composition according to Formula IX:

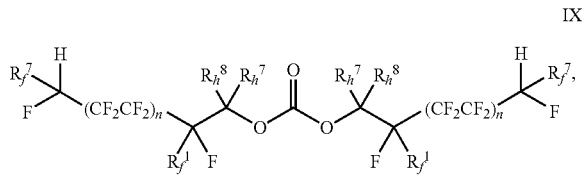

wherein each substituent is as defined above.

A few exemplary electrolyte solvent structures are shown below in Formulas X and XI:

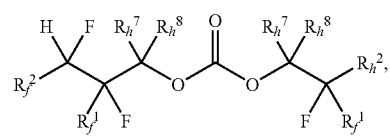

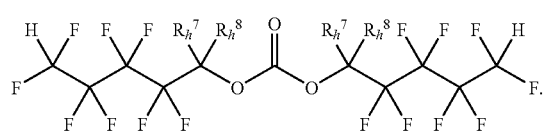

Lithium salts can be used together with the solvents disclosed herein. For example. Exemplary lithium salts are stable and soluble in the chosen charge-carrying media and perform well in the chosen lithium-ion cell, and include $LiPF_6$, $LiBF_4$, $LiClO_4$, lithium bis(oxalato)borate ("LiBOB"), $LiN(SO_2CF_3)_2$, $LiN(SO_2C_2F_5)_2$, $LiAsF_6$, $LiC(SO_2CF_3)_3$, and combinations thereof. Suitable cosolvents for mixing with the solvents of the present invention include those useful in lithium ion batteries, such as ethylene carbonate, propylene carbonate, dimethyl carbonate, diethyl carbonate, ethylmethyl carbonate, vinylene carbonate, vinylethylene carbonate, fluoroethylene carbonate or combination thereof.

Rechargeable lithium-ion cells or batteries generally comprise a positive electrode and a negative electrode with a separator therebetween, together with a charge-carrying electrolyte comprising a charge-carrying media or solvent or solvent mixture as provided in this disclosure along with a lithium salt. Suitable lithium salts include, for example, those described in the preceding paragraph.

Objects and advantages of this invention are further illustrated by the following examples, but the particular materials and amounts thereof recited in these examples, as well as other conditions and details, should not be construed to unduly limit this invention.

EXAMPLES

All numbers are weight percent (wt. %) unless otherwise noted.
Test Methods
A. Flammability The flammability of each compound was tested by placing approximately 5 mL of the compound in an aluminum weighing pan at room temperature and bringing a lighted wooden match to within about 1 mm of the sample surface. If the sample ignited it was given a rating of Yes (a). If the sample did not ignite after about ten seconds, the sample was then contacted with the lighted match. If the sample ignited, it was given a rating of Yes (b), but none of the samples earned this rating. If it did not ignite it was given a rating of No (b).
B. Solubility of $LiPF_6$ The proper proportions of $LiPF_6$ and the sample compound were combined at room temperature to make a solution containing 1.0 mole of $LiPF_6$ in 1.0 liter of the sample compound. If all of the $LiPF_6$ dissolved in the sample fluorinated compound, the $LiPF_6$ solubility is reported as "Yes". If a major fraction of the $LiPF_6$ remained undissolved, the solubility is reported as "No".
C. Accelerating Rate Calorimeter Exotherm Onset Temperature for Lithiated Silicon and Lithiated Graphite with Electrolytes.

C.1. Preparation of Lithiated Silicon and Lithiated Graphite

Silicon (−325 mesh, 1.04 $m^2/g$ BET surface area, Sigma-Aldrich, St. Louis, Mo.) (80%), Super-S carbon (12%, MMM Carbon, Belgium), polyvinylidene difluoride (PVDF), (8%, a 9% by weight solution in N-methylpyrrolidinone (NMP), NRC, Ottawa, Canada)) and NMP, (twice the mass of the silicon, Sigma-Aldrich) were milled into a slurry by mechanical milling in a modified Spex-8000 ball mill (including steel balls, 12.5 mm diameter, 1:10 mass ratio of silicon to steel balls) for 30 min. using 500 shakes/min. The slurry was spread in a thick layer on a glass plate and was heated for about 12 h in an oven set at 105° C. The dried coating was removed from the glass plate, ground in a mortar and pestle and the powder was passed through a 300 μm (50 mesh) screen. The BET surface area of this silicon electrode powder was 3.82 $m^2/g$. The silicon electrode powder (80±1 mg) and a circular piece of stainless steel mesh was pressed (96.5 MPa) into a silicon electrode pellet (14 mm diameter, 0.32 mm thick).

Ethylene Carbonate (EC), Diethyl Carbonate (DEC) and Lithium Hexafluorophosphate ($LiPF_6$) were obtained from EM Science (Gibbstown, N.J.). A 1 Molar (M) solution of $LiPF_6$ was prepared by dissolving the appropriate amount of $LiPF_6$ into the EC:DEC (1:2, v/v) solvent. Lithium bis(oxalato)borate (LiBOB) (Chemetall GmbH, Frankfurt, Germany), was dissolved in EC:DEC (1:2, v/v) to a saturated concentration of about 0.8M.

Coin cells (2325) were prepared with a silicon electrode pellet, lithium metal foil and 1M $LiPF_6$ EC:DEC (1:2 v/v) electrolyte and a separator. The cells were discharged using capacity control to form nominal $Li_1Si$, $Li_2Si$ and $Li_3Si$ (including irreversible capacity) using a current density of about 6.5 mA/g. After the discharge was completed, the coin cells were opened in an argon-filled glove box. The silicon electrode pellet was rinsed four times with dimethyl carbonate (DMC) and dried under reduced pressure to remove the residual DMC solvent.

Mesocarbon microbeads (MCMB) (E-One Moli/Energy Canada Ltd., Vancouver, BC), that had been heat-treated to about 2650° C., were used to prepare a graphite electrode powder by the same procedure used to prepare the silicon electrode powder. The average particle size of the MCMB was about 20 μm determined by scanning electron microscopy (SEM), and the BET specific surface area was 0.81 $m^2/g$. The BET surface area of the graphite electrode powder, after drying and sieving, was 1.82 $m^2/g$. Graphite electrode pellets (14 mm in diameter and 1 mm in thickness) were made using the same procedure as for the silicon electrode pellets, except that the graphite electrode pellets were about 300 mg in mass and did not include the stainless steel mesh. Coin cells assembled with the graphite electrode pellet, lithium metal foil, separator and 1M LiPF$_6$ EC:DEC electrolyte were discharged to form nominal Li$_{0.81}$C$_6$.

C.2. ARC Sample Preparation

The samples for the ARC Exotherm Onset Temperature test were prepared as described in Y. Wang, et al., Electrochemical and Solid State Letters, 9(7), A340-A343, (2006). The sample holder was made from 304 stainless steel seamless tubing with a wall thickness of 0.015 mm (0.006 inches) (Microgroup, Medway, Mass.). The outer diameter of the tubing was 6.35 mm (0.250 inches) and the length of pieces cut for the ARC sample holders was 39.1 mm (1.540 inches). The temperature of the ARC was set to 100° C. to start the test. The sample was equilibrated for 15 min., and the self-heating rate was measured over a period of 10 min. If the self-heating rate was less than 0.04° C./min., the sample temperature was increased by 10° C., at a heating rate of 5° C./min. The sample was equilibrated at this new temperature for 15 min., and the self-heating rate was again measured. The ARC Exotherm Onset Temperature was recorded when the self-heating rate was sustained above 0.04° C./min. The test was stopped when the sample temperature reached 350° C. or the self-heating rate exceeded 20° C./min. The results of these ARC tests with electrolytes prepared with Examples 1-4 and with Comparative Example 2 are displayed in Table 1.

D. ARC Exotherm Onset Temperature with delithiated LiCoO$_2$ and delithiated LiMn$_2$O$_4$ with Electrolytes.

LiCoO$_2$ (particle diameter approximately 5 μm) and LiMn$_2$O$_4$ were obtained from E-One Moli/Energy Canada Ltd. (Vancouver, BC). LiPF$_6$ (Stella Chemifa Corp., Osaka, Japan) was dissolved to a concentration of 1M in EC:DEC (1:2 v/v) solvent (available from Ferro Corp., Cleveland, Ohio).

A sample of delithiated LiCoO$_2$ was prepared in a standard 2325 coin cell. LiCoO$_2$ electrode powder was prepared by combining 7% each of Super S Carbon Black and PVDF, (10% in NMP, NRC, Ottawa, Canada) with about 300 mg of the LiCoO$_2$ powder. The NMP solvent was evaporated by heating the mixture at approximately 100° C. and the LiCoO$_2$ electrode powder was forced through a 50 mesh screen. LiCoO$_2$ electrode pellets were prepared by pressing the powder in a die. The pellets were about 18 mm in diameter and about 1 mm thick.

Coin cells (2325) with a LiCoO$_2$ electrode pellet, a stainless steel mesh electrode, a 1 M LiPF$_6$ EC/DEC (1:2 v/v) electrolyte and three polypropylene No. 2502 separators (Celanese Corp., Dallas, Tex.) were assembled in an argon-filled glove box. The cells were charged with a constant current of 1.0 mA until the cell voltage was 4.2 V vs. Li/Li$^+$. After reaching 4.2 V, the cells were allowed to remain at open circuit conditions for 30 minutes. The open circuit voltage was less than 4.2 V. The cells were charged with a constant current of 0.5 mA to 4.2 V versus Li/Li$^+$. After a total of four such charge-rest cycles, where the current in each cycle was reduced by 50% from the current used in the previous cycle, the charged cells were dissembled in a argon filled glove box. The delithiated LiCoO$_2$ electrode pellet was removed from the cell and was rinsed with dimethylcarbonate (DMC) four times. The pellet was placed in the glove box antechamber under reduced pressure for 2 h to remove the residual DMC. Finally, the sample was lightly ground for use in the ARC test.

A sample of delithiated LiMn$_2$O$_4$ was prepared by the same procedure as that used to prepare the delithiated LiCoO$_2$, but substituting LiMn$_2$O$_4$ powder.

The samples for the ARC Exotherm Onset Temperature test with delithiated LiCoO$_2$ and delithiated LiMn$_2$O$_4$ were prepared in the same manner as the samples for the ARC Exotherm Onset Temperature test with lithiated silicon, except that about 100 mg of either delithiated LiCoO$_2$ or delithiated LiMn$_2$O$_4$ was used with an equal mass of test electrolyte, and the temperature of the ARC was initially set to 110° C.

E. Charge Discharge Cycling of LiFePO$_4$/Li$_4$Ti$_5$O$_{12}$ and LiFePO$_4$/Graphite Cells Containing 0.5 M LiPF$_6$ Electrolytes.

Examples 1-4 were each tested neat in LiFePO$_4$/graphite and LiFePO$_4$/Li$_{4/3}$Ti$_{5/3}$O$_4$ coin cells. LiFePO$_4$ (from Phostech Lithium, Montreal, Canada). Li$_{4/3}$Ti$_{5/3}$O$_4$ was obtained from NEI Corp. (Piscataway, N.J.). The graphite used was mesocarbon microbeads (MCMB) heat treated to near 2650° C. Electrodes were made from the active materials, 10% by weight Super S Carbon Black and 10% by weight PVDF binder. LiFePO$_4$ and Li$_{4/3}$Ti$_{5/3}$O$_4$ electrodes were coated on aluminum foil and MCMB electrodes were coated on copper foil. A 20% capacity excess of the negative electrode was used in the cells, to ensure that the negative electrode had a stable and known potential versus Li/Li$^+$ when the Li-ion cell reached the fully charged state (i.e., Li$_0$FePO$_4$).

The electrolyte formulations were 0.5 M LiPF$_6$ in each of Examples 1-4 and Comparative Example 1. Coin cells (2325) employing Celgard No. 2502 separators were used as test vehicles. Cells were charged using currents corresponding to a normal recharge in 10, 20 or 40 h (C/10, C/20 or C/40) between the limits of 4.2 V and 2.5 V versus Li/Li$^+$.

Initial experiments identified those solvents that could sustain acceptable charge-discharge cycling. There was some indication that some of the electrolytes may not have fully wetted the separator and electrodes. Therefore experiments were repeated for the Example 1 where the electrodes and separators were "pressure wet". Pressure wetting was carried out by submerging the electrodes and separators in a vial of electrolyte, using a stainless steel weight to prevent floating. The vial was placed within a vacuum/pressure vessel, and the vessel was evacuated to approx-25 psi (172 kPa). After 30 seconds, the vessel was slowly pressurized to 120 psi (827 kPa). After an additional 30 seconds, the pressure was slowly released and the electrodes and separators were removed. Coin cells were then made with no additional electrolyte added.

F. Cycling of LiFePO$_4$/Silicon Alloy cells with 10% of Fluorinated Solvent in EC:DEC Base Cosolvent.

Preparation of Silicon Alloy

Aluminum, silicon, iron, titanium, and tin were obtained as pure elements in high purity (99.8 weight percent or greater) from Alfa Aesar, Ward Hill, Mass. or Aldrich, Milwaukee, Wis. A mixture of rare earth elements, also known as mischmetal (MM), was also obtained from Alfa Aesar with 99.0 weight percent minimum rare earth content which contained approximately 50% cerium, 18% neodymium, 6% praseodymium, 22% lanthanum, and 4% other rare earth elements.

The silicon alloy composition was prepared by melting a mixture of 7.89 g aluminum shot, 35.18 g silicon flakes, 9.34 g iron shot, 1.00 g titanium granules, 17.35 g tin shot, and 29.26 g mischmetal (MM) in an argon-filled arc furnace (from Advanced Vacuum Systems, Ayer, Mass.) with a copper hearth to produce an ingot. The ingot was cut into strips using a diamond blade wet saw.

The ingots were then further processed by melt spinning. The melt spinning apparatus included a vacuum chamber having a cylindrical quartz glass crucible (16 mm internal diameter and 140 mm length) with a 0.35 mm orifice that was positioned above a rotating cooling wheel. The rotating cooling wheel (10 mm thick and 203 mm diameter) was fabricated from a copper alloy (Ni—Si—Cr—Cu C18000 alloy from Nonferrous Products, Inc., Franklin, Ind.). Before processing, the edge surface of the cooling wheel was polished with a rubbing compound (Imperial Microfinishing from 3M, St. Paul, Minn.) and then wiped with mineral oil to leave a thin film.

After placing a 20 g ingot strip in the crucible, the system was first evacuated to 80 milliTorr (mT) and then filled with helium gas to 200 T. The ingot was melted using radio frequency induction. As the temperature reached 1350° C., 400 T helium pressure was applied to the surface of the molten alloy composition and the alloy composition was extruded through a nozzle onto the spinning (5031 revolutions per min.) cooling wheel. Ribbon strips were formed that had a width of 1 mm and a thickness of 10 μm. The ribbon strips were annealed at 200° C. for 2.5 h under an argon atmosphere in a tube furnace, then cooled and powdered.

Each of Examples 1-4 was used as an additive to the electrolyte in coin cells (2325) with an electrode of $LiFePO_4$ (from Phostech Lithium, Montreal, PQ, Canada), an electrode of the silicon alloy composition and No. 2502 Celgard separators. The silicon alloy electrodes were 92% silicon alloy, 2.2% Ketjen black, 5.5% polyimide PI2555 (HD Microsystems, Parlin, N.J.). The Ketjen Black and silicon alloy anode were premilled together using a Fritsch Micromill Pulverisette 7 (Goshen, N.Y.) planetary mill with four 13 micrometer diameter, tungsten carbide balls for thirty minutes at a setting of seven. $LiFePO_4$ electrodes were made from the active material, 4% Super S Carbon Black and 6% PVDF binder. $LiFePO_4$ electrodes were coated on aluminum foil. A 10% capacity excess of the negative electrode was used. This was to ensure that the negative electrode had a stable and known potential versus $Li/Li^+$ when the Li-ion cell reached the fully charged state (i.e., $Li_oFePO_4$).

Electrolytes used in the cells were 1M $LiPF_6$ in EC/DEC (1:2, v/v), with 10% of Examples 1-4.

The coin cells were charged and discharged between 2.5V and 3.7V using a C/10 rate (based on the positive electrode) for the first lithiation of the silicon alloy. For subsequent discharge/charge cycles, a C/5 rate (based on the positive electrode) was used. A trickle current of 10 mA/g (based on the active electrode mass of silicon alloy) for lithiation of the silicon alloy was used at the end of each C/5 charge of the cell. The cells remained at open-circuit for 15 min. rest between each charge and discharge.

Example 1

4-(1,1,2,3,3,3-hexafluoropropyl)-1,3-dioxolan-2-one

Example 1 was prepared by combining 2,2-dimethyl-1,3-dioxolane (200 g, 1.96 moles, Fluka Chemie GmbH, Deisenhofen, Germany) and Luperox 575 (10 g, 0.041 moles) (Arkema, Oakville, Ontario, Canada) were combined in a 600 mL Parr reactor (Parr Instrument Co., Moline, Ill.). The reactor was warmed to 75° C. and hexafluoropropene (300 g, 2.0 moles) (MDA Manufacturing Inc., Decatur, Ala.) was added at a constant rate. The reactor was allowed to stir at this temperature for 16 h. The crude reaction material was distilled using a ten plate Oldershaw column to afford 4-(1,1,2,3,3,3-hexafluoropropyl)-1,3-dioxolane (boiling point (b.p.) of 144° C.).

The above purified product (265.3 g, 1.05 moles) was combined with methanol (674 g, 21.03 moles) and concentrated hydrochloric acid (26.03 g, 0.71 moles) in a 3-L round bottom flask and the mixture was heated at reflux for 72 h. Excess methanol was removed by rotary evaporation. The resulting fluorochemical diol (116 g, 0.55 moles) was combined with pyridine (181 g, 2.3 moles) and dichloromethane (235 mL) in a 1-L round bottom flask. The temperature was maintained below 0° C. and phosgene solution (20% in toluene, 60 g phosgene, 0.60 moles) (Sigma-Aldrich, St. Louis, Mo.) was added dropwise from a jacketed addition funnel that was maintained at or below 0° C. Following the complete addition of the phosgene solution, the reaction mixture was allowed to warm to room temperature. The reaction mixture was quenched with excess saturated ammonium chloride. The organic phase was collected. The aqueous phase was extracted once with dichloromethane (200 mL). The organic phases were combined and washed with 1N hydrochloric acid, saturated, aqueous sodium hydrogen carbonate, saturated brine, dried with anhydrous sodium sulfate, filtered and concentrated via rotary evaporation. Components of the reaction mixture were separated on a one-plate distillation column.

The purified product was analyzed by Gas Chromatography/Mass Spectrometry (GC/MS). $MCMB/LiFePO_4$ coin cells (2325) made and cycled as per Test Method E with Example 1 as the only electrolyte solvent had a capacity fade rate of 2.65% capacity fade/cycle for a discharge rate of C/40 and a capacity fade rate of 0.62% capacity fade/cycle for a discharge rate of C/10.

Example 2

4-((1,1,2,3,3,3-hexafluoropropoxy)methyl)-1,3-dioxolan-2-one

Example 2 was prepared by combining 4-(hydroxymethyl)-1,3-dioxolan-2-one (100 g, 0.84 moles) (Huntsman, Salt Lake City, Utah) with potassium carbonate (23 g, 0.166 moles) and acetonitrile (200 mL) in a 600 mL Parr reactor. The reactor was warmed to 45° C. and hexafluoropropene (139 g, 0.92 moles) was added at a constant rate. The reactor was stirred until the decrease in pressure stopped. Volatile material was removed from the reaction mixture by rotary evaporation. The olefin of the desired product was present and was saturated by reaction with anhydrous HF at room temperature. Vacuum distillation was done to purify the product. The fraction that boiled at 145-150° C. at 3 T (0.4 kPa) was collected. The fraction was 97.5% pure. The product was analyzed by GC/MS and F-19 NMR. $MCMB/LiFePO_4$ coin cells (2325) made and cycled as per Test Method E with Example 2 as the only electrolyte solvent had high impedance, and the capacity fade rate could not be calculated.

Example 3

Ethyl 2,2,3,4,4,4-hexafluorobutyl carbonate

Example 3 was prepared by combining 2,2,3,4,4,4-hexafluorobutan-1-ol (184 g, 1.012 moles, Lancaster Synthesis Ltd., Ward Hill, Mass.), triethylamine (102 g, 1.008 moles) and methyl-t-butyl ether (350 mL) in a 1-L round bottom flask that was maintained at a temperature between 5° C. and 15° C. with a carbon dioxide/water bath. To the stirred mix, ethylchloroformate (100 g, 0.92 moles) was added from a jacketed addition funnel that was maintained between 5° C. and 15° C. The ethylchloroformate was added over a period of 4 h. Once addition was complete, the reaction mixture was stirred for an additional 16 h and was allowed to warm to room temperature. Then 100 mL of distilled water was added to the reaction mixture. The organic phase was collected. The water phase was extracted twice with 100 mL portions of methyl-t-butyl ether and all of the organic phases were combined. The organic phase was washed with a 100 mL portion of distilled water and a 100 mL portion of 1N HCl. The ether was removed by rotary evaporation. The remaining sample was purified by fractional distillation, using a concentric tube column. The product was analyzed by GC/MS.

Example 4

Methyl-2,2,3,4,4,4-hexafluorobutyl carbonate

In a predried, two-necked, 500 mL round bottom flask, flushed with nitrogen, and equipped with a thermocouple probe, Claisen adapter, magnetic stir bar, water-cooled condenser and addition funnel, 2,2,3,4,4,4-hexafluorobutan-1-ol (90.00 g, 0.4943 moles, Lancaster Synthesis Ltd., Ward Hill, Mass.), triethylamine (62.7 g, 0.6196 moles) and methyl-t-butyl ether (200 mL) were combined. At an initial temperature of 22° C., methylchloroformate (64.12 g, 0.6678 moles) was added dropwise, from the addition funnel, over a 1 h period. During the addition, the temperature rose to 60° C. A white precipitate formed during the reaction. After the complete addition of the methylchloroformate, the reaction mixture was stirred for about 18 h at ambient temperature. The reaction mixture was combined, with stirring, with a premixed solution of 200 mL of 1.023 N HCl and 300 mL of deionized water. The resulting mixture separated into two phases. The organic phase was washed sequentially with 400 mL of water, 400 mL of 5% $Na_2CO_{3(aq)}$, and two 400 mL portions of water. The organic phase was treated for 3 days with activated 3 A molecular sieves. The product was collected by fractional distillation, under nitrogen, at atmospheric pressure and a head temperature of 151.2-153.0° C. The product was analyzed by GC/MS and the purity was measured as 98.9% by GC-FID.

Each of the Examples 1-4 was rated "Yes" for solubility of $LiPF_6$.

Example 5

Bis(3,3,4,5,5,5-hexafluoropentan-2-yl) carbonate

Preparation of 3,3,4,5,5,5-hexafluoropentan-2-ol

A quantity of 3,3,4,5,5,5-hexafluoropentan-2-ol was prepared by combining absolute ethanol 200 proof (100 g, 2.17 moles, AAPER Alcohol and Chemical Co.) with t-amyl peroxy-2-ethylhexanoate (5 g, 0.021 moles) (available as Luperox 575 from Arkema, Oakville, Ontario, Canada) in a 600 mL Parr pressure reactor. The reactor was heated to 75° C. and hexafluoropropene (120 g, 0.8 moles) (MDA Manufacturing Inc., Decatur, Ala.) was added at a constant rate. The reactor was allowed to stir at this temperature for 16 h. The crude reaction material was distilled using a ten plate Oldershaw column to afford 150 g of 3,3,4,5,5,5-hexafluoropentan-2-ol (b.p.=121° C.).

In a 1-L, 3-neck round bottom flask, 3,3,4,5,5,5-hexafluoropentan-2-ol (150 g, 0.76 moles) was combined with pyridine (120 g, 1.51 moles) and 200 mL of methylene chloride. The mixture was stirred using an overhead stirrer and kept at a temperature of −15° C. using an ethylene glycol/$CO_2$ bath. Triphosgene (40 g, 0.13 moles) (TCI America, Portland, Oreg.) was dissolved in 200 mL of methylene chloride and added to the mix using a jacketed addition funnel maintained at −15° C. Following the addition of the triphosgene, the cooling bath was removed and the reaction mixture was allowed to warm to room temperature over a period of 24 h. Saturated aqueous ammonium chloride (250 mL) was added to the reaction mixture. The organic phase was collected. The aqueous phase was extracted with one 200 mL portion of methylene chloride. The organic portions were combined and washed with a 100 mL portion of 1N HCl, 100 mL of saturated sodium hydrogen carbonate and 100 mL portion of deionized water. A volatile fraction was removed by rotary evaporation. The remaining fraction was distilled and the

TABLE 1

Results

| | | | ARC Exotherm Onset Temperature | | | |
|---|---|---|---|---|---|---|
| Example | Flammable | Cell Cycle Additive (a) | Charged $Li_xSi$ Anode (b) | Charged $LiCoO_2$ Cathode | Charged Graphite Anode | Charged $Li_2MnO_4$ Cathode |
| 1 | No (b) | similar to 1:2 EC/DEC | (+) | 230° C. | 175° C. | 210° C. |
| 2 | No (b) | similar to 1:2 EC/DEC | (+) | 230° C. | 210° C. | 220° C. |
| 3 | No (b) | Lower than 1:2 EC/DEC | (=) | 210° C. | No Data | 130° C. |
| 4 | No (b) | Lower than 1:2 EC/DEC | (=) | 240° C. | No Data | 150° C. |
| Comparative Example (1:2 EC:DEC) | Yes (a) | 46% Capacity retention at 100th cycle | (−) | 140° C. | 90° C. | No Data |
| EC | No (b) | | (=) | 140° C. | | 150° C. |

Notes:
(a) Cell Cycle Life as 10% Additive to 1:2 EC:DEC (1M LiPF6), Silicon Alloy/LiFePO4 positive
(b) (+) means that the Exotherm Onset Temperature is higher than when EC is used, (=) means that the Exotherm Onset Temperature is the same as when EC is used same as EC, (−) means that the Exotherm Onset Temperature is lower than when EC is used.

fraction boiling at 105-107° C. and 2.66 kPa was collected. The product was verified by GC/MS.

Example 6

4-(1,1,2,3,3,3-hexafluoropropyl)-1,3-dioxan-2-one

Example 6 was prepared by combining 1,3-dioxan-2-one (240 g, 2.35 moles) (Richman Chemical Inc., Lower Gwynedd, Pa.) with benzoyl peroxide (5 g, 0.02 moles) in a 600 mL Parr reactor. The reactor was heated to 73° C. and hexafluoropropene (16 g, 0.1066 moles) was fed into the reactor over a 2 h period. The reactor was maintained at the set temperature for an additional 24 h. The reactor contents were collected and analyzed by GC/MS.

Various modifications and alterations of this invention will become apparent to those skilled in the art without departing from the scope and principles of this invention, and it should be understood that this invention is not to be unduly limited to the illustrative embodiments set forth hereinabove.

The invention claimed is:

1. A lithium ion battery comprising:
   a liquid electrolyte;
   a positive electrode; and
   a negative electrode,
   wherein said liquid electrolyte comprises a solvent and a lithium salt wherein the solvent comprises a compound according to the formula R—O—C(=O)—O—R',
   wherein R is $C_xH_{2x+1}$ and x is an integer from 1 to 4, and wherein R' is —$C(R_h^7)(R_h^8)CFR_f^1(CF_2CF_2)_nCHFR_f^7$, wherein $R_f^1$ is fluorine or $C_pF_{2p+1}$ and p is an integer from 1 to 4, $R_f^7$ is F, $C_pF_{2p+1}$, or $R_f^3O(R_f^4O)_m$—, wherein $R_f^3$ is $C_yF_{2y+1}$, and y is an integer from 1 to 8, and $R_f^4$ is $C_qF_{2q}$, wherein q is an integer from 1 to 4, and $R_h^7$ and $R_h^8$ are independently H or an alkyl group and wherein $R_h^7$ and $R_h^8$ are not both alkyl groups, the alkyl groups having 1 to 4 carbon atoms, m is 0 or 1, and n is 0 or 1, and such that when $R_h^7$ and $R_h^8$ are both hydrogen and n is 0, then $R_f^7$ is not fluorine.

2. The lithium ion battery of claim 1 wherein $R_h^7$ and $R_h^8$ are both hydrogen and n is zero.

3. The lithium ion battery of claim 1 wherein one of $R_h^7$ and $R_h^8$ is an alkyl group, n is 1, and both $R_f^1$ and $R_f^7$ are fluorine.

4. The lithium ion battery of claim 1 wherein one of $R_h^7$ and $R_h^8$ is an alkyl group, n is zero, and $R_f^1$ is F or $C_nF_{2n+1}$, and $R_f^7$ and $R_h^8$ are F, $C_nF_{2n+1}$, or $R_f^3O(R_f^4O)_m$—.

* * * * *

UNITED STATES PATENT AND TRADEMARK OFFICE
CERTIFICATE OF CORRECTION

PATENT NO. : 8,435,679 B2
APPLICATION NO. : 12/519461
DATED : May 7, 2013
INVENTOR(S) : William M. Lamanna et al.

It is certified that error appears in the above-identified patent and that said Letters Patent is hereby corrected as shown below:

In the Specification

Column 2
Line 12, delete "caronate" and insert --carbonate--

Column 3
Line 8, delete "$R_f^3O(R_f^4O)_m$" and insert --$R_f^3O(R_f^4O)_m$-- --
Line 11, delete "$R_h^3$ and $R_h^{a}$" and insert --$R_h^2$ and $R_h^3$--
Lines 15-16, delete "-$C(R_h^7)(R_h^8)_nCFR_f^1(CF_2CF_2)_nCHFR_f^7$"
and insert -- -$C(R_h^7)(R_h^8)CFR_f^1(CF_2CF_2)_nCHFR_f^7$--

Column 6
Line 2, delete "$C(R_h^7)(R_h^8)_nCFR_f^1(CF_2CF_2)_nCHFR_f^7$"
and insert --$C(R_h^7)(R_h^8)CFR_f^1(CF_2CF_2)_nCHFR_f^7$--
Lines 57-58, delete "$C(R_h^7)(R_h^8)_nCFR_f^1(CF_2CF_2)CHFR_f^7$"
and insert --$C(R_h^7)(R_h^8)CFR_f^1(CF_2CF_2)_nCHFR_f^7$--

Column 7

Lines 16-24 Formula X delete " 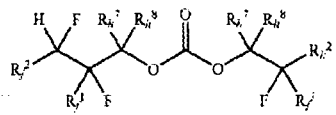 " and insert -- 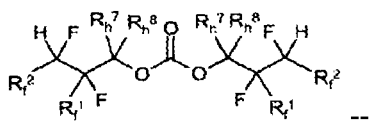 --

Column 8
Line 40-41, delete "bis(oxolato)borate" and insert --bis(oxalate)borate--

Signed and Sealed this
Twenty-sixth Day of November, 2013

Margaret A. Focarino
*Commissioner for Patents of the United States Patent and Trademark Office*